(12) United States Patent
Hübner et al.

(10) Patent No.: US 9,005,622 B2
(45) Date of Patent: Apr. 14, 2015

(54) CELL WALL COMPONENTS OF ENTEROCOCCI AND USES THEREOF

(75) Inventors: Johannes Hübner, Freiburg (DE); Christian Theilacker, Freiburg (DE); Otto Holst, Bad Oldesloe (DE); Zbigniew Kaczynski, Gdansk (PL)

(73) Assignees: Forschungszentrum Borstel, Borstel (DE); Universitätsklinikum Freiburg, Freitburg (DE)

( * ) Notice: Subject to any disclaimer, the term of this patent is extended or adjusted under 35 U.S.C. 154(b) by 0 days.

(21) Appl. No.: 12/739,646

(22) PCT Filed: Jan. 19, 2010

(86) PCT No.: PCT/EP2010/000285
§ 371 (c)(1),
(2), (4) Date: Aug. 17, 2010

(87) PCT Pub. No.: WO2011/088843
PCT Pub. Date: Jul. 28, 2011

(65) Prior Publication Data
US 2012/0282268 A1    Nov. 8, 2012

(51) Int. Cl.
| | |
|---|---|
| *A61K 39/02* | (2006.01) |
| *A61K 31/715* | (2006.01) |
| *A61K 39/09* | (2006.01) |
| *A61K 31/726* | (2006.01) |
| *C07H 15/04* | (2006.01) |

(52) U.S. Cl.
CPC .............. *A61K 39/09* (2013.01); *A61K 31/715* (2013.01); *A61K 31/726* (2013.01); *C07H 15/04* (2013.01)

(58) Field of Classification Search
USPC ............................... 424/9.1, 9.2, 184.1, 234.1
See application file for complete search history.

(56) References Cited

U.S. PATENT DOCUMENTS 5,989,542 A * 11/1999 Pier et al. .................... 424/93.48
6,756,361 B1 * 6/2004 Fattom et al. ................... 514/54
2003/0113350 A1 * 6/2003 Fattom et al. .............. 424/243.1
2005/0009121 A1    1/2005 Talaga
2006/0121058 A1    6/2006 Malley

OTHER PUBLICATIONS

Andrzejet et al. 1993 (Structure of the O-specific polysaccharide containing pentitol phosphate, isolated from *Hafnia alvei* strain PCM 1191 lipopolysaccharide; European Journal of Biochemistry, 213(3):1255-60).*
Hsu et al. 2006 (Immunochemical characterization of polysaccharide antigesn from six clinical strains of Enterococci; BMC Microbiology, 6:62).*
Kaczynski et al. 2009 (Structural Characterisation of Polysaccharides Isolated from Cell Wall of *Enterococcus faecalis*, University of Gdansk, Fault of Chemistry, Jul. 2009).*
Gamien et al. 1993 (Structure of the O-specific polysaccharide containing pentitol phosphate isolated from *Hafnia alvei* strain PCM 1191 lipopolysaccharide; Eur. J. Biochem. 213:1255-1260).*
Hsu et al. 2006 (Immunochemical characterization of polysaccharide antigens from six clinical strains of Enterococci; BMC Microbiology; 6:62; pp. 1-9).*
Huebner et al. 1999 (Isolation and chemical characterization of a capsular polysaccharide antigen shared by clinical isolates of *Enterococcus faecalis* and Vancomycin-Resistant *Enterococcus faecium*; Infection and Immunity, 67(3):1213-1219).*
Koch et al. 2004 (Enterococcal infections: host response, therapeutic and prophylactic possibilities; Vaccine, 22:822-830).*
Hsu, C.T., et al., "Immunochemical characterization of polysaccharide antigens from six clinical strains of Enterococci," *BMC Microbiology*, Jul. 12, 2006, pp. 62-70, vol. 6.
Takada, H., et al., "Molecular and structural requirements of a lipoteichoic acid from *Enterococcus hirae* ATCC 9790 for cytokine-inducing, antitumor, and antigenic activities," *Infection and Immunity*, Jan. 1995, pp. 57-65, vol. 63, No. 1.
Kaczyński, Z., et al., "Structural Characterisation of Polysaccharides Isolated From Cell Wall of *Enterococcus faecalis*," University of Gdańsk, Faculty of Chemistry, Jul. 2009, Abstract only.

* cited by examiner

*Primary Examiner* — Ja'Na Hines
*Assistant Examiner* — Mary Lyons
(74) *Attorney, Agent, or Firm* — Saliwanchik, Lloyd & Eisenschenk

(57) ABSTRACT

The present invention relates to enterococcal cell wall components and their uses in the prevention and therapy of bacterial infection.

1 Claim, 3 Drawing Sheets

CELL WALL COMPONENTS OF ENTEROCOCCI AND USES THEREOF

CROSS REFERENCE TO A RELATED APPLICATION

This application is a National Stage Application of International Application Number PCT/EP2010/000285, filed Jan. 19, 2010; which is incorporated herein by reference in its entirety.

The present invention relates to enterococcal cell wall components and their uses in the prevention and therapy of bacterial infection. For the purposes of the present invention, all references as cited herein are incorporated in their entireties.

BACKGROUND OF THE INVENTION

At least 15 enterococci species exist, but only two of them are commonly associated with clinical infection, namely, *Enterococcus faecalis*, which is responsible for 80% infections caused by enterococci, and *Enterococcus faecium*. The Gram-positive bacterium *Enterococcus faecalis* is a natural inhabitant of the mammalian gastrointestinal tract, and is commonly found in soil, sewage, water, and food, frequently through faecal contamination (Klare, I., Werner, G. and Witte, W. Contrib. Microbiol. 2001, 8, 108-22).

Enterococci are important nosocomial pathogens causing a variety of infections including nosocomial bacteremia, endocarditis, as well as urinary tract, surgical wound, and foreign body infections.

Sensitive strains of these bacteria can be treated with ampicillin and vancomycin. Nevertheless, some enterococci are intrinsically resistant to β-lactam-based antibiotics (some penicillins and virtually all cephalosporins) as well as many aminoglycosides. In the last two decades, particularly virulent strains of *Enterococcus* that are resistant to vancomycin (Vancomycin-resistant *Enterococcus*, or VRE) have emerged in nosocomial infections of hospitalized patients especially in the US. The increasing occurrence of enterococcal strains resistant to multiple antibiotics underscores the necessity to improve the understanding of the pathogenesis of infection (Murray, B. E. N. Engl. J. Med. 2000, 342, 710-721; Theilacker, C., Krueger, W. A., Kropec, A. and Huebner, J. Vaccine 2004, 22 Suppl 1, S31-8).

Teichoic acids can be found in the cell wall of gram-positive bacteria, such as *Staphylococci, Streptococci, Bacillus, Clostridium, Corynebacterium* and *Listeria*, and appear to extend to the surface of the peptidoglycan layer. Teichoic acids are not found in the gram-negative bacteria.

They can be covalently linked to N-acetylmuramic acid of the peptidoglycan layer, to the lipids of the cytoplasmic membrane, or to a terminal D-alanine in the tetrapeptide crosslinks between N-acetylmuramic acid units.

The main function of teichoic acids is to provide rigidity to the cell-wall by attracting cations such as magnesium and sodium. Teichoic acids are usually, but not always, substituted with D-alanine ester residues, giving the molecule zwitterionic properties. These zwitterionic teichoic acids are suspected ligands for toll-like receptors 2 and 4. Teichoic acids also assist in regulation of cell growth by limiting the ability of autolysins to break the β(1-4) bond between the N-acetyl glucosamine and the N-acetylmuramic acid. Teichoic acids serve as an attachment site for some parasites. Destruction of the bacteria and release of the teichoic acid into the bloodstream may cause fever, blood vessel dilation and possibly shock and subsequent death. Teichoic acid can also be used by bacteria to attach to mucosal membranes.

Lipoteichoic acid (LTA) is a major constituent of the cell wall of Gram-positive bacteria. It consists of teichoic acids, long chains of glycerol or ribitol phosphate and is anchored to the lipid bilayer via a glyceride. LTA bound to targets can interact with circulating antibodies and activate the complement cascade to induce a passive immune kill phenomenon.

Teichoic acids and lipoteichoic acids have been considered strong exogenous pyrogens, i.e. they belong to the substances that may lead to a feverish reaction in a human after a bacterial infection by gram-positive bacteria. They are most likely recognized by the toll-like receptor TLR-2 that is expressed on monocytes and dendritic cells, B- and T-lymphocytes and macrophages. Furthermore, they lead to the excretion of cytokines, and therefore are one factor for the inflammatory reaction following such an infection.

Due to their antigenic properties, they have also been proposed as interesting candidates for the development of synthetic vaccines.

U.S. Pat. No. 7,011,826 describes a vaccine for the prevention of lactic acidosis in a vertebrate, said vaccine comprising at least one isolated microorganism, or fragment or fragments thereof, wherein said microorganism is capable of producing lactic acid within the gut of said vertebrate, and wherein said microorganism is selected from the group consisting of: *Clostridium*-like species, *Prevotella*-like species, *Bacteroides*-like species, *Enterococcus*-like species, *Selenomonas* species.

In order to provide more efficient strategies to effectively treat and/or prevent infection in vertebrates caused, at least in part, by enterococci, new antigenic bacterial targets are needed which could both be used in new and improved vaccination strategies, as well as in the development and production of respective vaccines.

As a part of the search for carbohydrate virulence factors and the development of alternative treatments such as glycoconjugate vaccines to combat enterococcal infections, the present invention fulfils these need by providing new capsular polysaccharides, wall lipoteichoic acids and lipoteichoic acids isolated from the cell wall of enterococci.

Thus, the objects of the present invention in a first aspect thereof are solved by an enterococcal cell wall component consisting of

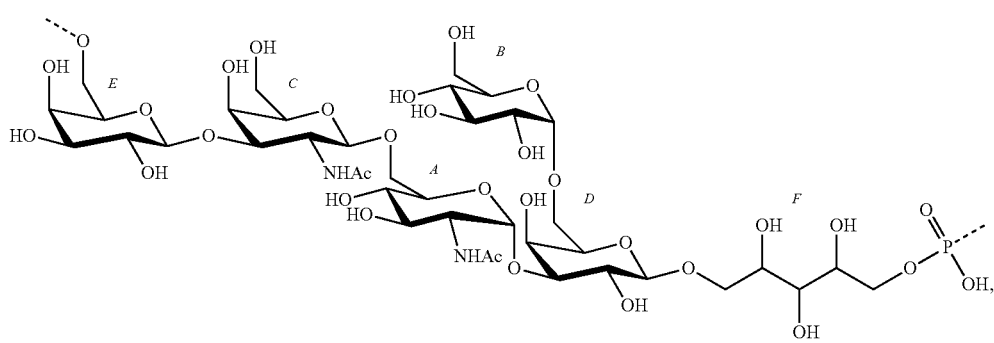

(I)

and modified derivatives thereof, and pharmaceutically acceptable salts thereof.

This enterococcal cell wall component (in the following also designated as "enterococcal antigen") provides a new antigenic target for the development of more efficient strategies to effectively treat and/or prevent infection in vertebrates caused, at least in part, by enterococci, allow for improved vaccination strategies, and allow the development and production of respective vaccines, such as glycoconjugate vaccines.

According to the present invention, the term a "modified derivative" or "modified derivatives" shall include chemically or enzymatically modified enterococcal antigens according to the formula I as above, wherein said modified derivative maintains its function as an enterococcal antigenic determinant and/or to the same, or substantially the same, extent as the enterococcal antigen according to formula I. Preferably, said modified derivative exhibits a quantitatively increased immunological reaction, compared to a non-modified enterococcal antigen. Such increase of the immunological reaction can be detected with immunological assays known in the art.

Examples for modified derivatives are preferably compounds of formula I that are modified to include a linker group in order to be coupled or conjugated to other chemical entities. These linker groups are known in the state of the art, and usually are immunologically inactive, i.e. do not interfere with the immunological properties of the enterococcal antigen. Other modifications include the addition of chemical moieties of the enterococcal antigen in order to carry a detectable label, such as chelating groups or enzymatic groups. Furthermore, peptide (e.g. His) or other "labels" or "tags" can be added in order to be able to purify and/or use the enterococcal antigen in diagnostic assays.

Finally, the enterococcal antigen can include chemical modifications, for example at the rings of the sugar components of the enterococcal antigen, wherein the antigen can be modified to replace an existing side group with either H, an unsubstituted, monosubstituted or polysubstituted $C_1$-$C_{18}$-alkyl, wherein said alkyl can be straight, branched or cyclic, alkenyl, an unsubstituted, monosubstituted or polysubstituted aryl or heteroaryl residue, an unsubstituted, monosubstituted or polysubstituted benzene group, an acyl group, such as formyl, acetyl, trichloroacetyl, fumaryl, maleyl, succinyl, benzoyl, or a branched or heteroatom or aryl substituted acyl group, an alkoxy substituent, such as —OMe, —OEt, —OnPr, -iPr, —OnBu, —OiBu, —OsecBu, —OtBu, whose alkyl group can be branched, straight or cyclic, an alkyl group bound via a sulphur atom such as —SMe, —SEt, or a sulfonyl group, such as —$SO_3H$, —$SO_2Me$, —$SO_2CF_3$, —$SO_2C_6H_4CH_3$ or $SO_2C_6H_4CH_2Br$, or a nitrogen substituent, such as $NH_2$, NHR, —NRR' (with R, R'=alkyl, alkenyl or aryl as above), NC or —$NO_2$, or fluoro, chloro, bromo, iodine, —CN or a heterosubstituent. As mentioned above, these derivatives are preferably included in order to improve the solubility of the antigen, increase the immunological effect of said antigen (preferably quantitatively), and/or to allow the compound to be coupled to other moieties, e.g. in order to be coupled to a surface (such as a well or chip), and/or to be used in diagnostic assays.

Another aspect of the invention relates to a method for producing the enterococcal cell wall component according to the present invention, wherein said method comprises isolating said enterococcal cell wall component from a bacterial fraction, or comprising synthesizing said antigen, at least in part, through chemical synthesis. Isolation can include purifying said cell wall component from bacterial fractions to be substantially free of other bacterial components, but can also include the isolation as part of certain bacterial fractions, such as cell wall fractions including other parts of the cellular wall, as described herein.

Another aspect of the invention relates to an antibody, preferably a monoclonal antibody or antigenic fragment thereof, that specifically recognizes an enterococcal antigen according to the present invention. The term "antibody" shall include both monoclonal or polyclonal antibodies, recombinant antibodies or fragments thereof, such as Fab and the like, as well as human or humanized antibodies.

Another aspect of the invention then relates to a method for producing the antibody according to the present invention, comprising immunizing a mammal, preferably a rabbit, with an enterococcal cell wall component according to the present invention, or a with the pharmaceutical composition according to the present invention, and preferably the vaccine according to the present invention. Respective methods are known to the person of skill, and are disclosed in the state of the art.

Yet another aspect of the present invention then relates to a method for producing the antibody according to the present invention, comprising generating hybridoma cells producing said antibody as a monoclonal antibody, or comprising a recombinant production of said antibody in a host cell. Respective methods are known to the person of skill, and are disclosed in the state of the art Still another important aspect of the present invention then relates to the use of the enterococcal antigen according to the present invention as an antigen in the production of antibodies that are specific for said antigen.

Another aspect of the invention then relates to a pharmaceutical composition, comprising at least one enterococcal antigen according to the present invention and/or at least one antibody according to the present invention, together with a pharmaceutically acceptable carrier and/or excipient.

Particularly preferred is a pharmaceutical composition according to the present invention, wherein said composition comprises a cell wall component according to formula I, namely a WTA.

Further preferred is a pharmaceutical composition according to the present invention, wherein said composition is formulated as a vaccine, in particular against infections caused by enterococci, in particular antibiotic resistant enterococci, such as VRE strains, preferably of E. faecalis. Most preferred is a pharmaceutical composition according to the present invention, wherein said cell wall component according to formula I is present in a glycoconjugate vaccine.

The WTA according to the present invention (either present as the antigen alone or in an extract or bacterium as described herein) is preferably used for an enterococci-vaccine, either for active or passive immunization.

Thus, according to the invention, there is provided a pharmaceutical composition, and in particular a vaccine, for the prevention of enterococcal infections in a vertebrate, said pharmaceutical composition comprising at least one new enterococcal antigen according to the present invention, optionally together with a pharmaceutically acceptable carrier, adjuvants and/or diluent.

Typically, the vaccine can comprise live or dead intact cells of at least one enterococcal strain, preferably of E. faecalis, comprising the enterococcal antigen of the invention. More typically, the vaccine comprises cell lysate from at least one of said enterococcal strains as comprising the enterococcal antigen or antigens. Even more typically, the vaccine comprises a crude enterococcal antigen mixture or purified a enterococcal antigen or enterococcal antigens from at least one of said enterococcal strains, preferably E. faecalis. Still more typically, the vaccine comprises a fraction of the cell wall and associated proteins as enterococcal antigen of at least one of said enterococcal strains. The vaccine may also be comprised of a combination of one of the components. Most preferred is a glycoconjugate vaccine comprising an enterococcal antigen according to the present invention. Another aspect relates to a pharmaceutical composition or vaccine, wherein the enterococcal antigen as included has been produced, at least in part, through chemical synthesis. The methods for purifying the selected bacterial fractions containing enterococcal antigens are known to the person of skill, and further described herein.

Typically, the vertebrate is a monogastric, herbivore or ruminant animal or human subject. Even more typically, the vertebrate is selected from the group consisting of human, non-human primate, murine, bovine, ovine, equine, porcine, caprine, leporine, avian, feline and canine. More typically, the vertebrate is selected from the group consisting of human, ovine, camelids, porcine, bovine, equine or canine.

The pharmaceutical composition can be formulated for administration via intramuscular, subcutaneous, topical or other parenteral route. In general, the microorganisms of the present invention are commensal in nature. Thus, oral administration is generally not an effective route of vaccination, and as a consequence, administration via an intramuscular, subcutaneous topical or other parenteral route is preferred. The vaccine may also include cytokines, such as: G-CSF, GM-CSF, interleukins or tumour necrosis factor alpha, used singly or in combination.

The pharmaceutical composition may also include an adjuvant. More typically, the adjuvant is selected from the group consisting of Freunds Complete/Incomplete Adjuvant, Montenide Macrol Adjuvant, Phosphate Buffered Saline and Mannan oil emulsions, saponins (QuiLA) dextran (dextran sulphate, DEAE-Dextran), aluminum compounds (Imject Alum), N-acetylglucosamiyl-N-acetylmuramyl-L-alanyl-D-isoglutamine (Gerbu adjuvant). More typically, the adjuvant is selected from the group as described in the Vaccine 1995, vol 13, p 1203; 1993 vol 11 p 293; and 1992 vol 10 p 427, the disclosures of which are incorporated herein by reference.

Yet another important aspect of the present invention then relates to an enterococcal cell wall component (enterococcal antigen) according to the present invention, the antibody according to the present invention, or the pharmaceutical composition according to the present invention for use in the treatment of diseases, such as bacterial infections, in particular enterococcal infection, such as nosocomial bacteremia infection, endocarditis, urinary tract infections, surgical wound infections, and foreign body infections.

Yet another important aspect of the present invention then relates to the use of the enterococcal cell wall component according to the present invention, the antibody according to the present invention, or the pharmaceutical composition according to the present invention (i.e. the enterococcal antigens) for the treatment against bacterial infections or for the preparation of a medicament against bacterial infections, in particular enterococcal infection, such as nosocomial bacteraemia infection, endocarditis, urinary tract infections, surgical wound infections, and foreign body infections, in particular caused by antibiotic resistant enterococci, such as VRE strains, such as E. faecalis.

According to yet another preferred embodiment of the invention, there is provided a method for inducing an immune response against at least one enterococcal strain comprising the enterococcal antigen of the present invention in a vertebrate, said method comprising administering to said vertebrate an immunologically effective amount of the vaccine in accordance with the invention, or a pharmaceutical composition in accordance with the invention.

According to yet another preferred embodiment of the invention, there is provided a method for treating or preventing a bacterial infection in a vertebrate, comprising administering to said vertebrate a therapeutically effective amount of the enterococcal cell wall component according the present invention, the antibody according to the present invention, or the pharmaceutical composition according to the present invention.

Preferred is a method according to the present invention, wherein said bacterial infection is an enterococcal infection, such as nosocomial bacteraemia infection, endocarditis, a urinary tract infection, surgical wound infection, and foreign body infection, and is particular caused by antibiotic resistant enterococci, such as a VRE strain, and in particular E. faecalis.

The present invention will now be further described in the following preferred non-limiting examples with reference to the accompanying figures, wherein FIG. 1 shows the $^1$H NMR spectra of capsular polysaccharides isolated from E. faecalis: a)—type 2 strain, b)—type 5 strain. The letters refer to the carbohydrate residues as shown in FIG. 2, and the arabic numerals refer to the protons in the respective residues.

FIG. 2 shows the chemical structure of the repeating unit of the capsular polysaccharide isolated from type 2 strain of E. faecalis. The capsular polysaccharide isolated from type 5 strain possessed a highly similar structure lacking the O-acetyl group at position C-5 of $\beta$-D-Galf.

FIG. 3 shows the $^1$H NMR spectrum of lipoteichoic acids isolated from E. faecalis strain 12030. The letters refer to the glycerol residue and the glucose residues in kojibiose (FIG. 4), and the arabic numerals refer to the protons in the respective residues. The peaks for the protons belonging to the glucose residues substituted by alanine are found at about 4.4 and 4.65 ppm.

EXAMPLES

Capsular Polysaccharides

Capsular polysaccharides from type 2 and type 5 strains of *E. faecalis* (Maekawa S., Yoshioka M., and Kumamoto Y. Microbiol Immunol. 1992, 36, 671-81) were obtained by enzyme treatment of peptidoglycan with lysozyme and mutanolysin. Contaminating nucleic acid and proteins were removed by digestion with RNAse, DNAse and Proteinase K. The material was fractionated by gel-permeation chromatography (GPC) on Sephacryl S-400 and large molecular mass material was applied on a Sepharose Q column and eluted by a linear gradient on NaCl. The isolated polysaccharides were studied by sugar analysis, one-dimensional ($^1$H and $^{13}$C), and two-dimensional homonuclear $^1$H-$^1$H(COSY, TOCSY and NOESY) and heteronuclear $^1$H-$^{13}$C (HMQC, HMQC-TOCSY and HMBC) magnetic resonance spectroscopy (NMR). All 1D and 2D spectra were recorded with Bruker DRX Avance 600 MHz spectrometer.

Figure 1:
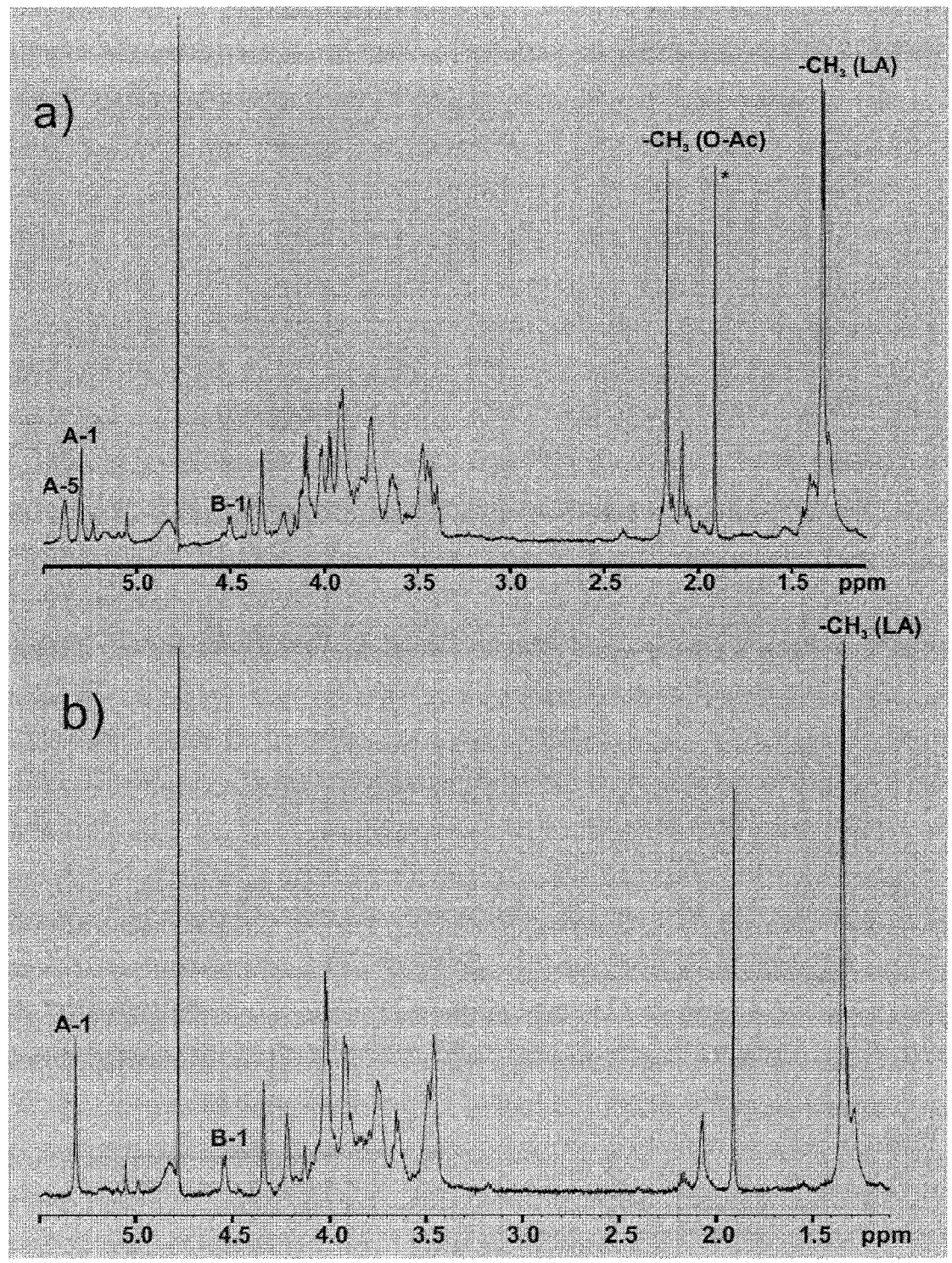

The $^1$H NMR spectrum of capsular polysaccharides from type 2 (FIG. 1*a*) showed two anomeric signals (residue A, [$^3J_{H1,H2}$<2 Hz]; residue B, [$^3J_{H1,H2}$=7.8 Hz]), which were identified as β-D-Galf and β-D-Glcp, respectively. In addition, a broad signal at d 5.4 was identified, which was assigned to proton H-5 of β-D-Galf due to substitution at C-5 by the O-acetyl group. Furthermore, the doublet at δ 1.3 was recognized as methyl group belonging to a lactic acid (LA) residue. The sequence of the residues in the repeating units was established by NOESY and HMBC experiments.

Figure 2:
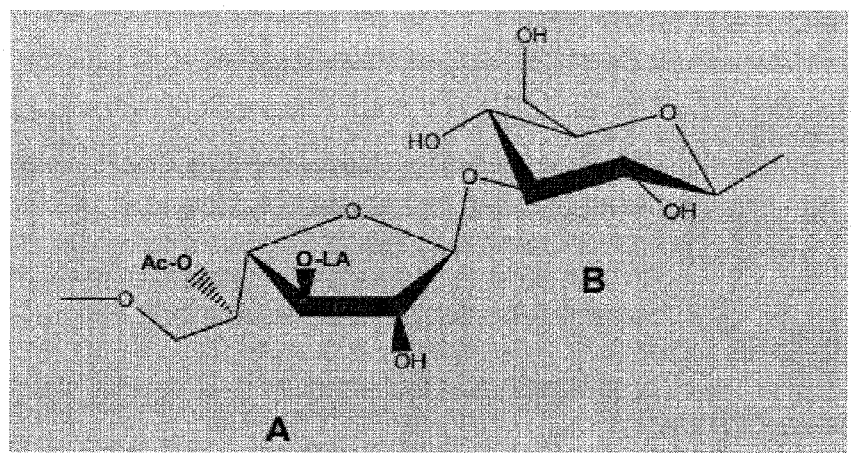

In capsular polysaccharides isolated from type 5 strain of *E. faecalis*, the O-acetyl group at C-5 of D-Galf was missing (FIG. 2).

The present invention thus revealed the presence of two novel capsular polysaccharides in *E. faecalis*.

Lipoteichoic Acids

Lipoteichoic acids from strain 12030 of *E. faecalis* (Hufnagel, M., Hancock, L. E. Koch, S., Theilacker, C., Gilmore, M. S, and Huebner, J. J. Clin. Microbiol. 2004, 42, 2548-57) were obtained by disruption of bacterial cells with glass beads, followed by extraction with n-butanol. After phase partition the water phase was lyophilized and resuspended in chromatography starting buffer. Hydrophobic interaction chromatography (HIC) was performed on octyl-sepharose. Phosphorus-containing fractions eluting around 50% PrOH were pooled and repeatedly lyophilized until complete evaporation of the eluent.

Figure 3:
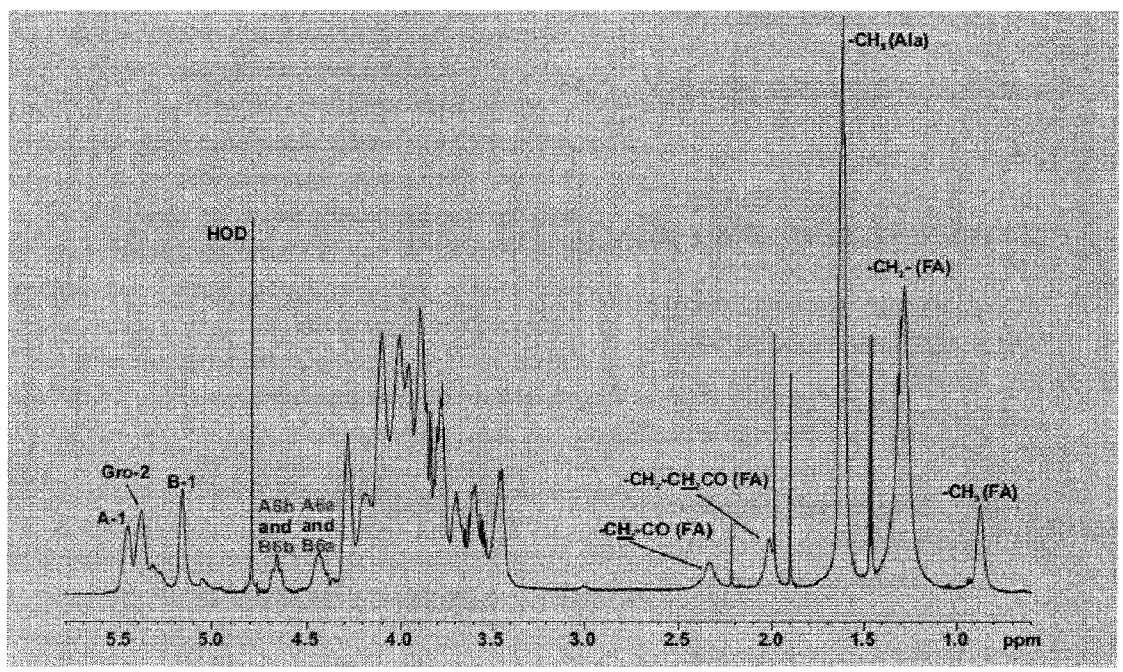

The $^1$H NMR spectrum of lipoteichoic acids from strain 12030 of *E. faecalis* (FIG. 3) showed two anomeric signals, which were identified as substituted at position C-2, and terminal glucose residues, respectively. In addition, a signal at δ 5.4 was assigned to proton H-2 of the glycerol residue. The strong deshielding of this proton is caused by substitution at position C-2 by an alanine residue. The doublet at δ 1.6 was recognized as a methyl group belonging to an alanine residue. Furthermore, signals characteristic for fatty acids were identified.

Figure 4:
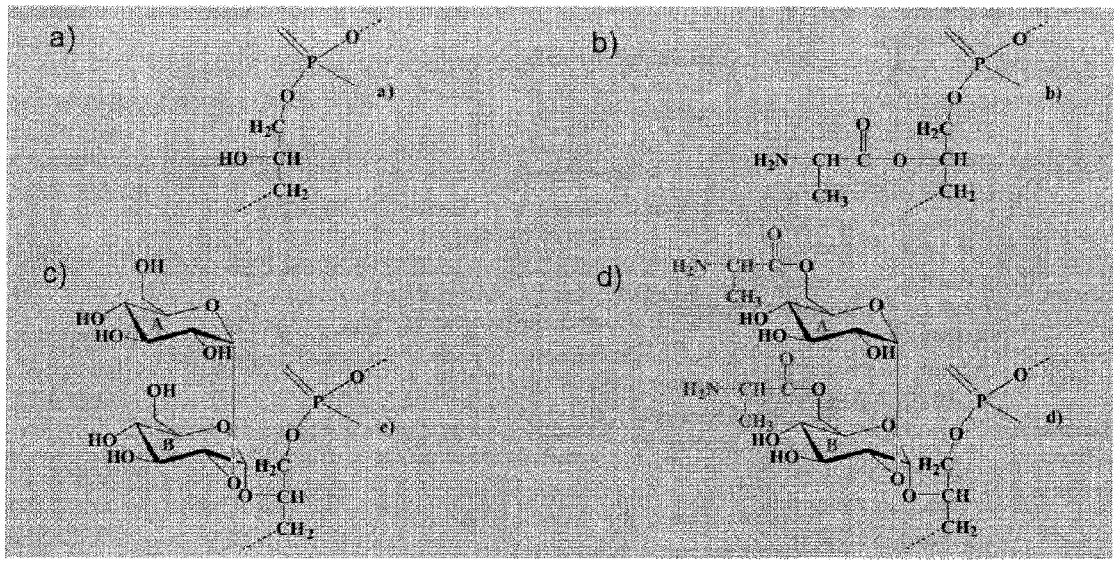
FIG. 4 shows the chemical structures of different repeating units of lipoteichoic acids isolated from strain 12030 of *E. faecalis*.

The NMR results confirmed some of the structures of lipoteichoic acids proposed by Wicken and Baddiley (Wicken, A. J. and Baddiley, J. Biochem J. 1963, 87, 54-62), namely, 1,3-poly(glycerol phosphate), and 1,3-poly(glycerol phosphate) substituted at the position C-2 of glycerol residues with alanine, or kojibiose (FIG. 4). In addition, substitution by alanine was localized at positions C-6 of both glucoses in the kojibiose residue (FIG. 4), establishing a novel lipoteichoic acid structure in enterococci.

Wall Teichoic Acids (WTA)

WTA according to the present invention was isolated from bacterial cell walls of *E. faecalis*. The mixture of polysaccharides was fractionated an purified by GPC (Sephacryl S-200) and anion exchange chromatography (Sepharose Q).

Figure 5:
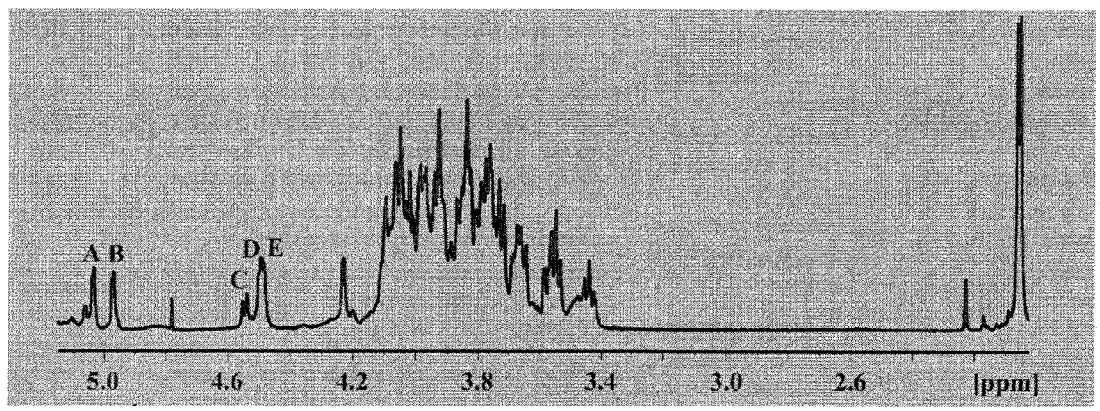
FIG. 5 shows the $^1$H NMR spectrum of wall teichoic acid (WTA) according to the invention as isolated from *E. faecalis*. The letters refer to the sugar residue (FIG. 6).

Compositional analyses identified Glc, Gal, GlcNAc, GalNAc, and ribitol as main constituents of WTA. The $^1$H NMR spectrum of WTA showed in the anomeric region five major peaks (FIG. 5). The $^{31}$P NMR spectrum showed one signal, which was assigned to a phosphate group bridging ribitol and Galp ($^1$H, $^{31}$P HMQC NMR experiment).

Figure 6:
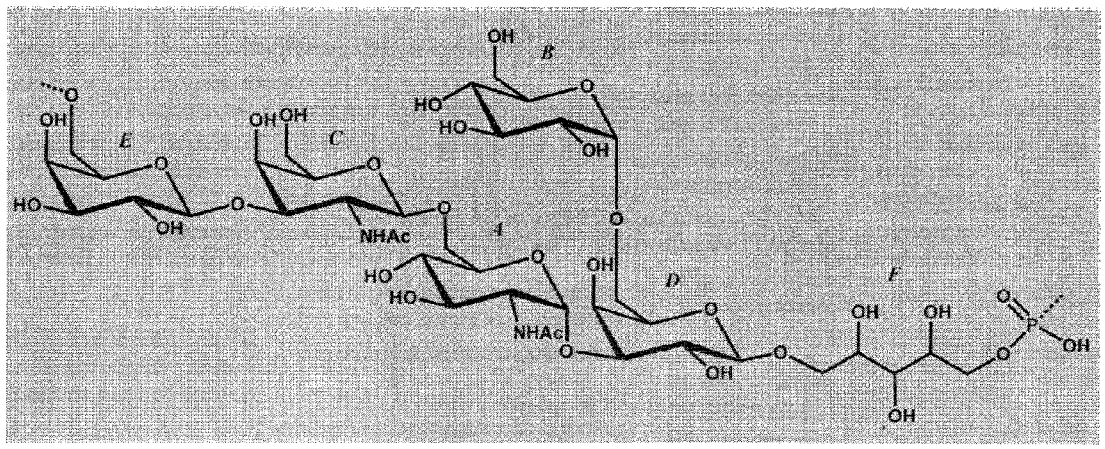
FIG. 6 shows the chemical structure of the repeating unit of WTA isolated from *E. faecalis* according to the present invention.

The sequence of the residues in the repeating units of the WTA according to the invention of *E. faecalis* is shown in FIG. 6.

The invention claimed is:

1. A method for inducing an immune response against at least one antibiotic resistant enterococcal strain in a vertebrate, said method comprising administering to said vertebrate an immunologically effective amount of an isolated compound selected from the group consisting of:

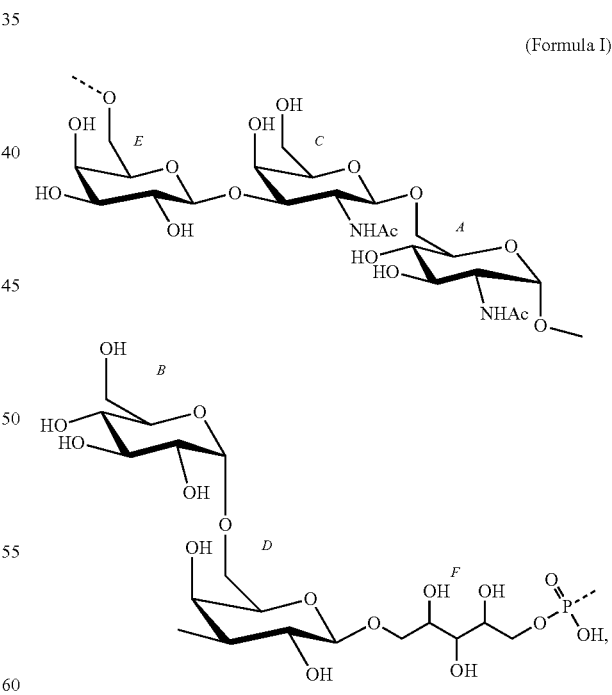

(Formula I)

wherein at least one of the rings of the sugar components is modified to replace an existing side group with either H; an unsubstituted, monosubstituted or polysubstituted C1-C18-alkyl, wherein said alkyl is selected from the group consisting of straight, branched or cyclic alkenyl; an unsubstituted, monosubstituted or polysubstituted aryl or heteroaryl residue; an unsubstituted, monosubstituted or polysubstituted benzene group; an acyl group; a branched or heteroatom or aryl substituted acyl group; an alkoxy substituent whose alkyl group can be branched, straight or cyclic; an alkyl group bound via a sulphur atom or a sulfonyl group; an alkyl group bound via a nitrogen substituent; or an alkyl group bound via fluoro, chloro, bromo, iodine, —CN or a heterosubstituent, and pharmaceutically acceptable salts thereof; wherein said isolated compound is administered to said vertebrate by a route selected from the group consisting of intramuscular, subcutaneous, topical and other parenteral routes.

* * * * *